United States Patent [19]

Throckmorton

[11] Patent Number: 4,471,153
[45] Date of Patent: Sep. 11, 1984

[54] PROCESS FOR THE REMOVAL OF CYCLOPENTADIENE FROM UNSATURATED $C_5$-HYDROCARBONS

[75] Inventor: Morford C. Throckmorton, Akron, Ohio

[73] Assignee: The Goodyear Tire & Rubber Company, Akron, Ohio

[21] Appl. No.: 529,462

[22] Filed: Sep. 6, 1983

[51] Int. Cl.³ .............................................. C07C 7/01
[52] U.S. Cl. .................................. 585/850; 585/832; 585/864
[58] Field of Search ................ 585/850, 830, 832, 864

[56] References Cited

U.S. PATENT DOCUMENTS

| | | | |
|---|---|---|---|
| 3,510,405 | 5/1970 | Takao et al. | 585/832 |
| 3,557,239 | 1/1971 | Gebbart et al. | 585/832 |
| 3,723,551 | 3/1973 | Kohler et al. | 585/830 |
| 3,911,040 | 10/1975 | Shelton et al. | 585/830 |
| 4,310,388 | 1/1982 | Volkamer et al. | 585/864 |

FOREIGN PATENT DOCUMENTS

| | | | |
|---|---|---|---|
| 769326 | 6/1971 | Belgium | 585/864 |
| 41-17743 | 10/1966 | Japan | 585/832 |

Primary Examiner—Delbert E. Gantz
Assistant Examiner—A. Pal
Attorney, Agent, or Firm—Alvin T. Rockhill

[57] ABSTRACT

The presence of cyclopentadiene in unsaturated $C_5$-hydrocarbons is often very undesirable. This is because cyclopentadiene is a poison to many of the catalysts used to polymerize $C_5$-hydrocarbon monomers. This invention reveals a process for reducing the concentration of cyclopentadiene in impure unsaturated $C_5$-hydrocarbons containing cyclopentadiene, comprising adding to said impure unsaturated $C_5$-hydrocarbon (a) at least one member selected from the group consisting of trialkylaluminum compounds, dialkylaluminum hydride compounds, dialkylmagnesium compounds, and dialkylzinc compounds; and (b) an organonickel compound.

17 Claims, No Drawings

PROCESS FOR THE REMOVAL OF CYCLOPENTADIENE FROM UNSATURATED C₅-HYDROCARBONS

TECHNICAL FIELD

This invention relates to a method for the removal of cyclopentadiene from unsaturated $C_5$-hydrocarbon streams. It is particularly beneficial in the purification of unsaturated $C_5$-hydrocarbon monomers, such as, isoprene and piperylene (that is 1,3-pentadiene) which are to be polymerized utilizing Ziegler catalysts or ionic catalysts.

BACKGROUND OF THE INVENTION

Various unsaturated $C_5$-hydrocarbons are useful as monomers for polymerization into a variety of useful polymers. Isoprene and piperylene are examples of $C_5$-hydrocarbon monomers that are frequently utilized in the synthesis of a variety of synthetic rubbers. Unfortunately, unsaturated $C_5$-hydrocarbon streams are often contaminated with cyclopentadiene (CPD). The presence of cyclopentadiene in $C_5$-hydrocarbon streams is very undesirable since cyclopentadiene is harmful to Ziegler catalysts, Szwarc catalysts, and ionic catalysts. Thus, the presence of cyclopentadiene in a $C_5$-monomer is detrimental to many of the catalysts commonly employed to polymerize such $C_5$ monomers. For example, cyclopentadiene poisons the titanium catalysts commonly used to polymerize isoprene into polyisoprene.

Many techniques are known for the purification of organic compounds. One of the most widely used of these purification techniques is fractional distillation. However, fractional distillation cannot generally be employed to effectively separate cyclopentadiene from unsaturated $C_5$-hydrocarbons. This is because cyclopentadiene forms azeotropes with unsaturated $C_5$-hydrocarbons, for instance, isoprene.

Other more sophisticated techniques for the purification of organic compounds are also known. For example, U.S. Pat. No. 3,647,913 discloses a process for purifying olefinic hydrocarbon streams containing acetylenes and cumulative diolefins as impurities. This technique involves selectively polymerizing the acetylenes and cumulative diolefins in the hydrocarbon stream into solids by contacting them with a two-component catalyst system wherein the first component is a compound of a metal of Group IA, IIA, IIB, or IIIA, and wherein the second compound is a compound of a transition metal of Group IVB, VB, VIB, VIIB, or VIII of the Periodic Table. However, this patent does not specify a technique for the removal of cyclopentadiene from an unsaturated $C_5$-hydrocarbon. In fact, the catalyst disclosed by this reference cannot generally be used to polymerize cyclopentadiene into a solid.

U.S. Pat. No. 4,009,126 describes a technique for removing acetylenic impurities from organic compounds utilizing a zinc ferrite catalyst composition.

U.S. Pat. No. 4,035,433 describes a technique for the removal of acetylenic impurities from olefinic hydrocarbon streams by selective oxidation using a copper chromite catalyst.

SUMMARY OT THE INVENTION

This invention utilizes organonickel compounds in its technique for reducing the concentration of cyclopentadiene in unsaturated $C_5$-hydrocarbon streams. This invention further discloses the unique ability of organonickel compounds when used in conjunction with certain alkylaluminum compounds, or alkylzinc compounds to remove unwanted cyclopentadiene from unsaturated $C_5$-hydrocarbons.

This invention specifically discloses a process for reducing the concentration of cyclopentadiene in an impure unsaturated $C_5$-hydrocarbon containing cyclopentadiene as an impurity comprising adding to said impure unsaturated $C_5$-hydrocarbon (a) at least one member selected from the group consisting of trialkylaluminum compounds, dialkylaluminum hydride compounds, dialkylmagnesium compounds, and dialkylzinc compounds; and (b) an organonickel compound.

This invention also reveals a process for the purification of impure unsaturated $C_5$-hydrocarbons containing cyclopentadiene as an impurity comprising (1) adding to said impure unsaturated $C_5$-hydrocarbon (a) at least one member selected from the group consisting of trialkylaluminum compounds, dialkylaluminum hydride compounds, dialkylmagnesium compounds, and dialkylzinc compounds; and (b) an organonickel compound, in amounts and under conditions sufficient to convert the cyclopentadiene to a cyclopentadiene reaction product; followed by (2) fractionally distilling said impure unsaturated $C_5$-hydrocarbon under conditions sufficient to separate the cyclopentadiene reaction product from the $C_5$-hydrocarbon.

DETAILED DESCRIPTION OF THE INVENTION

This invention can be used for reducing the concentration of unwanted cyclopentadiene in impure unsaturated $C_5$-hydrocarbons containing unwanted quantities of cyclopentadiene. The unsaturated $C_5$-hydrocarbons in which this invention is most valuable are olefinic hydrocarbons containing one or more double bonds. Generally, this invention will find its greatest utility in reducing the concentration of cyclopentadiene in diolefins containing two double bonds, such as isoprene and piperylene.

This invention is based on the discovery that organonickel compounds can be used in conjunction with certain aluminum, magnesium, or zinc compounds to convert cyclopentadiene in an unsaturated $C_5$-hydrocarbon into a cyclopentadiene reaction product without adversely affecting the other $C_5$-hydrocarbons. The cyclopentadiene reaction product formed has properties which allow it to be removed from the $C_5$-hydrocarbon by simple means. For example, the cyclopentadiene reaction product formed can be removed from the unsaturated $C_5$-hydrocarbon by fractional distillation, chelation, or absorption onto a material such as activated charcoal.

The cyclopentadiene reaction product into which the cyclopentadiene is converted has not been identified. However, it is theorized that perhaps the cyclopentadiene is dimerized into dicyclopentadiene or that the cyclopentadiene complexes with the nickel to form a nickelocene type of structure. In any case, it is known that the cyclopentadiene is not polymerized into a high molecular weight solid material.

Unsaturated $C_5$-hydrocarbons which have been treated by the process of this invention which contain cyclopentadiene reaction product can normally be polymerized without poisoning the polymerization catalyst. In other words, the cyclopentadiene reaction product formed does not generally harm Ziegler catalysts, Szwarc catalysts, and ionic catalysts used to polymerize unsaturated C$_5$-hydrocarbons. Thus, cyclopentadiene is converted to a reaction product which is normally harmless to most polymerization catalysts. Even though it is normally possible to conduct polymerizations in the presence of the cyclopentadiene reaction product it will not normally be desirable to do so. In many applications, it is highly desirable, if not essential, to utilize relatively pure unsaturated C$_5$-hydrocarbons.

Cyclopentadiene in an impure unsaturated C$_5$-hydrocarbon can be converted into a cyclopentadiene reaction product by simply contacting the impure C$_5$-hydrocarbon with (a) at least one member selected from the group consisting of trialkylaluminum compounds, dialkylaluminum hydride compounds, dialkylmagnesium compounds, and dialkylzinc compounds; and (b) an organonickel compound.

The alkyl groups in the aluminum compounds, zinc compounds, and magnesium compounds generally contain from 1 to 30 carbon atoms. It is generally preferred for these alkyl groups to contain from 2 to 8 carbon atoms. Some representative example of trialkylaluminum compounds that can be used in the practice of this invention include: triethylaluminum (TEAL), tri-n-propylaluminum, triisobutylaluminum (TIBAL), and trihexylaluminum. Some representative examples of dialkylaluminum hydride compounds include: diisobutylaluminum hydride (DIBA-H), diethylaluminum hydride, and di-n-propylaluminum hydride. Some representative examples of dialkylzinc compounds that can be utilized in the practice of this invention include: diethylzinc, di-n-propylzinc, and dibutylzinc.

The organonickel compound used in the practice of this invention should be soluble in the unsaturated C$_5$-hydrocarbon being treated. Nickel salts of carboxylic acids containing from 4 to 30 carbon atoms are generally utilized for this purpose. Some representative examples of organonickel compounds that can be utilized include: nickel benzoate, nickel naphthenate, nickel-2-ethylhexanoate (which is commonly referred to as nickel octanoate or nickel octoate (NiOct), nickel neodecanoate, nickel acetylacetonate, and nickel salicylaldehyde.

The ratio between the amount by weight of the aluminum, magnesium, or zinc compound to the amount of organonickel compound employed generally ranges between about 1:1 and about 10:1. It is generally preferred for the ratio of the aluminum, magnesium, or zinc compound to the organonickel compound to range from 2:1 to 6:1. It is generally more preferred for the mole ratio of the aluminum compound, zinc compound, or magnesium compound to the organonickel compound to range between 3:1 and 5:1.

In the practice of this invention at least 0.3 moles of organonickel compound should be employed per mole of cyclopentadiene present in the unsaturated C$_5$-hydrocarbon being treated. In most cases it will not be advantageous to employ a mole ratio of organonickel compound to cyclopentadiene of greater than 20:1. Normally it is preferred for the ratio of organonickel employed to the amount of cyclopentadiene in the C$_5$-hydrocarbon being treated to range from 2:1 to 10:1, with the most preferred ratio ranging between 3:1 and 6:1.

The process of contacting the C$_5$-hydrocarbon being treated with (a) an alkylaluminum compound, an alkylzinc compound, or an alkylmagnesium compound; and (b) an organonickel compound can be effectuated by simply adding them to the C$_5$-hydrocarbon. This treatment may take place in the presence or absence of solvents for the unsaturated C$_5$-hydrocarbon being treated. This treatment can be carried out on either a batchwise basis or continuously. This treatment process can be carried out over a very wide temperature range. Even though temperature is not critical to this process, a temperature ranging from about $-20°$ C. to about $150°$ C. is normally utilized. In most cases a treatment temperature ranging from $15°$ C. to $60°$ C. will be preferred. Similarly, the time period in which the cyclopentadiene containing C$_5$-hydrocarbon is in contact with the alkylaluminum, alkylmagnesium, or alkylzinc compound and the organonickel compound can be varied over a wide range, suitably from about one minute to about 24 hours. The preferred time of contacting (treatment) is from about 5 minutes to about 2 hours.

The cyclopentadiene reaction product formed in the above-described treatment can be removed from the C$_5$-hydrocarbon by utilizing various physical and chemical techniques. For example, the cyclopentadiene reaction product formed can be removed from an unsaturated C$_5$-hydrocarbon by fractional distillation using techniques known to those skilled in the art.

This invention is illustrated by the following examples which are merely for the purpose of illustration and which are not to be regarded as limiting the scope of the invention or manner in which it can be practiced. Unless specifically indicated otherwise all parts and percentages are given by weight.

EXAMPLES 1 THROUGH 7

Fifty milliliters of an impure isoprene stream to which cyclopentadiene had been added was added to a series of 118 ml (4 ounce) bottles. The impure isoprene in these bottles was sparged with nitrogen to remove any dissolved oxygen. The concentration of cyclopentadiene in each of the samples is indicated in Table I as original CPD concentration and is given in ppm (parts per million).

An alkylaluminum compound and nickel octoate which were dissolved in hexane were added to each of the samples by injection with a syringe, except for example 6 wherein diethylzinc was substituted for the alkylaluminum compound. The amount of alkylaluminum compound or diethylzinc added is indicated in Table I. The amount of nickel octoate added is also indicated in Table I. The bottles were then capped and heated in a constant temperature bath at $50°$ C. for 30 minutes. Five milliliters of water was then added to each of the bottles. The bottles were then placed in refrigeration. The contents of each of the bottles was decanted and filtered with the filtrate being analyzed by gas-liquid chromatography to determine the concentration of any remaining cyclopentadiene. The concentration of cyclopentadiene in each of the samples after treatment by the process of this invention is indicated in Table I as is the percentage of cyclopentadiene removed.

TABLE I

| Example | Reagents Added$^a$ | Original CPD Conc.,ppm | CPD Conc. After Treatment | % CPD Removed |
|---|---|---|---|---|
| 1 | 2 TEAL/ 0.22 NiOct | 187 | 17 | 91 |
| 2 | 2 TEAL/ 0.44 NiOct | 186 | 7 | 96 |

TABLE I-continued

| Example | Reagents Added[a] | Original CPD Conc.,ppm | CPD Conc. After Treatment | % CPD Removed |
| --- | --- | --- | --- | --- |
| 3 | 3 TEAL/ 0.66 NiOct | 228 | 15 | 94 |
| 4 | 2 TIBAL/ 0.44 NiOct | 186 | 6 | 97 |
| 5 | 2 DIBA-H/ 0.44 NiOct | 186 | 13 | 93 |
| 6 | 2 Et$_2$Zn/ 0.44 NiOct | 186 | 3 | 98 |
| 7 | 5 Et$_2$Zn/ 1.30 NiOct | 363 | 0 | 100 |

[a]The compounds added are identified in abbreviated form as indicated below. The amount of the compound added is indicated as the number preceding the compounds designation and is given in millimoles.
TEAL = triethylaluminum
TIBAL = triisobutylaluminum
DIBA-H = diisobutylaluminum hydride
Et$_2$Zn = diethylzinc
NiOct = nickel octoate These examples clearly demonstrate the ability of the process of this invention to remove cyclopentadiene from impure isoprene. In all of these examples over 90 percent of the cyclopentadiene present was removed. In Example 7, which utilizes diethylzinc and nickel octanoate, 100 percent of the cyclopentadiene present was removed. After being treated by the process of this invention each of the seven samples tested contained less than 20 ppm of cyclopentadiene.

EXAMPLES 8 THROUGH 13

The procedure specified in Examples 1 through 7 was repeated in these experiments with the exception that longer reaction times were utilized in Examples 9–13. In Example 9 the contents of the bottle were allowed to react for 3 hours before addition of the water (in Examples 1 through 7 the contents were only allowed to react for 30 minutes). In Examples 10–13 the contents of the bottles were allowed to react for 18 hours before the reaction was stopped by addition of the water. These experiments were conducted in order to ascertain the relationship between the amount of nickel octoate added and the percentage of cyclopentadiene removed. The results of this series of experiments are summarized in Table II.

TABLE II

| Example | Reagents Added[a] | Original CPD Conc.,ppm | CPD Conc. After Treatment | % CPD Removed |
| --- | --- | --- | --- | --- |
| 8 | 3 TEAL/ 0.66 NiOct | 244 | 15 | 94 |
| 9 | 3 TEAL/ 0.33 NiOct | 244 | 14 | 94 |
| 10 | 1.5 TEAL/ 0.17 NiOct | 244 | 28 | 88 |
| 11 | 1.5 TEAL/ 0.08 NiOct | 244 | 99 | 58 |
| 12 | 0.75 TEAL/ 0.08 NiOct | 244 | 97 | 60 |
| 13 | 0.75 TEAL/ 0.04 NiOct | 244 | 137 | 43 |

[a]The compounds added are identified in abbreviated form as indicated below. The amount of the compound added is indicated as the number preceding the compounds designation and is given in millimoles.
TEAL = triethylaluminum
NiOct = nickel octoate This series of experiments indicates that the amount of cyclopentadiene removed is related to the amount of organonickel compound added to the impure isoprene. The addition of larger quantities of nickel octoate resulted in increases in the amount of cyclopentadiene removed. In Example 13 the mole ratio of nickel octoate added to cyclopentadiene present in the impure isoprene was 0.32 and only 43 percent of the cyclopentadiene originally present was removed. In Example 12 this ratio of nickel octoate to cyclopentadiene was increased to 0.64 and 60 percent of the cyclopentadiene originally present was removed. In Example 10 the ratio of nickel octoate to cyclopentadiene was 1.3 with 88 percent of the cyclopentadiene originally present being removed. When this ratio of nickel octoate to cyclopentadiene was increased to 2.6 the amount of cyclopentadiene removed was further increased to 94 percent.

EXAMPLES 14 THROUGH 21

The following series of experiments were conducted in order to demonstrate the unique ability of organonickel compounds to remove cyclopentadiene from C$_5$-hydrocarbons which is not demonstrated by other organometallic compounds. This series of experiments was done utilizing the procedure used in Example 2 except that various organometallic compounds were substituted for the nickel octoate utilized in Example 2. Triethylaluminum was utilized as the alkylaluminum compound in this series of experiments. The results of this series of examples is summarized in Table III.

TABLE III

| Example | Reagents Added[a] | Original CPD Conc.,ppm | CPD Conc. After Treatment | % CPD Removed |
| --- | --- | --- | --- | --- |
| 14 | 2 TEAL/ 0.44 CrOct | 186 | 193 | 0 |
| 15 | 2 TEAL/ 0.44 CoOct | 186 | 138 | 26 |
| 16 | 2 TEAL/ 0.44 CuNaph | 186 | 146 | 22 |
| 17 | 2 TEAL/ 0.44 FeOct | 186 | 164 | 12 |
| 18 | 2 TEAL/ 0.44 MnOct | 186 | 140 | 25 |
| 19 | 2 TEAL/ 0.44 V(AcAc)$_3$ | 173 | 167 | 3 |
| 20 | 3 TEAL/ 0.66 Sn(Oct)$_2$ | 228 | 233 | 0 |
| 21 | 4.5 TEAL/ 1.0 Zr(AcAc)$_4$ | 373 | 390 | 0 |

[a]The compounds added are identified in abbreviated form as indicated below. The amount of the compound added is indicated as the number preceding the compound designation and is given in millimoles.
CrOct = Chromium octoate
CoOct = Cobalt octoate
CuNaph = Copper naphthenate
FeOct = Iron octoate
MnOct = Manganese octoate
V(AcAc)$_3$ = Vanadium acetylacetonate
Sn(Oct)$_2$ = Tin octoate
Zr(AcAc)$_4$ = Zirconium acetylacetonate It is very apparent after examining Table III that chromium, cobalt, copper, iron, maganese, vanadium, tin, or zirconium cannot be employed in organometallic compounds as substitutes for the organonickel compounds used in the process of this invention. All of the organometallic compounds substituted for organonickel compounds in these examples (Examples 14–21) were ineffective for use in the removal of cyclopentadiene from isoprene. The cobalt compound tested did the best job of removing cyclopentadiene and it only removed 26 percent. In addition to this, the cobalt compound polymerized enough of the isoprene so as to transform it into a moderately viscous liquid. Thus, even if cobalt was effective at cyclopentadiene removal it would nevertheless be unacceptable for use because it would ruin the isoprene monomer by causing it to polymerize. This is in contrast to the use of nickel compounds which result in very little or no loss of isoprene during the treatment process of this invention.

EXAMPLE 22

Example 22 was conducted in order to demonstrate the ability of the process of this invention to remove cyclopentadiene from piperylene. A relatively crude piperylene stream containing about 41 percent trans-1,4-pentadiene, about 31 percent cis-1,4-pentadiene, about 16 percent cyclopentene, about 11 percent other olefins and unknowns, and about 1700 ppm of 1,3-cyclopentadiene was used in this experiment. This impure piperylene sample was refluxed at a temperature of 42° C. for one hour in the presence of 31 millimoles of tri-n-propyl-aluminum and 6 millimoles of nickel octoate. The sample was then analyzed for cyclopentadiene by using gas-liquid chromatography. This analysis indicated the presence of only 2 ppm of cyclopentadiene in the treated sample. Thus, the amount of cyclopentadiene present was reduced form about 1700 ppm to only 2 ppm which represents a reduction in the concentration of cyclopentadiene of greater than 99 percent.

EXAMPLES 23-29

The following series of experiments were conducted in order to demonstrate the unique ability of organonickel compounds to remove cyclopentadiene from impure piperylene which is not demonstrated by other metal salts. This series of experiments was done utilizing the procedure specified in Example 22 except that various metal salts were substituted for the nickel octoate utilized in Example 22. The metal salt that was used in place of nickel octoate is listed in Table IV. The cyclopentadiene concentration deteced after treatment and the percent of cyclopentadiene removed are so indicated in Table IV.

TABLE IV

| Example | Metal Salt | CPD Conc. After Treatment | % CPD Removed |
|---|---|---|---|
| 23 | FeOct | 1400 | 18 |
| 24 | CoOct | 1300 | 23 |
| 25 | CrNaph | 1800 | 0 |
| 26 | MnOct | 1300 | 23 |
| 27 | CuDec | 1700 | 0 |
| 28 | MoOct | 1700 | 0 |
| 29 | CeOct | 1500 | 12 |

FeOct = Iron Octoate
CoOct = Cobalt Octoate
CrNaph = Chromium naphthenate
MnOct = Manganese Octoate
CuDec = Copper neo-decanoate
MoOct = Molybdenum octoate
CeOct = Cerium octoate It is very apparent after examining Table IV that iron, cobalt, chromium, manganese, copper, molybdenum and cerium cannot be employed in organometallic compounds as substitutes for the organonickel compounds used in the process of this invention. All of the metal salts substituted for nickel octoate in these examples (Examples 23-29) were ineffective for use in the removal of cyclopentadiene from piperylene. This is, of course, in contrast to the organonickel compound used in Example 22 which was very effective for reducing the concentration of cyclopentadiene in impure piperylene.

While certain representative embodiments and details have been shown for the purpose of illustrating the invention, it will be apparent to those skilled in this art that various changes and modifications may be made therein without departing from the scope of the invention.

What is claimed is:

1. A process for reducing the concentration of cyclopentadiene in an impure unsaturated $C_5$-hydrocarbon containing cyclopentadiene as an impurity, comprising adding to said impure unsaturated $C_5$-hydrocarbon (a) at least one member selected from the group consisting of trialkylaluminum compounds, dialkylaluminum hydride compounds, dialkylmagnesium compounds, and dialkylzinc compounds, and (b) an organonickel compound.

2. A process as specified in claim 1 wherein the alkyl groups in said trialkylaluminum compounds, dialkylaluminum hydride compounds, dialkylmagnesium compounds, and dialkylzinc compounds contain from 1 to 30 carbon atoms.

3. A process as specified in claim 2 wherein the alkyl groups in said trialkylaluminum compounds, dialkylaluminum hydride compounds, dialkylmagnesium compounds, and dialkylzinc compounds contain from 2 to 10 carbon atoms.

4. A process as specified in claim 1 wherein said members selected from the group consisting of trialkylaluminum compounds, dialkylaluminum hydride compounds, dialkylmagnesium compounds, and dialkylzinc compounds are selected from the group consisting of triethylaluminum, tri-n-propylaluminum, triisobutylaluminum, trihexylaluminum, diisobutylaluminum hydride, diethylaluminum hydride, di-n-propylaluminum hydride, diethylzinc, di-n-propylzinc, and dibutylzinc.

5. A process as specified in claim 4 wherein said members selected from the group consisting of trialkylaluminum compounds, dialkylaluminum hydride compounds, dialkylmagnesium compounds, and dialkylzinc compounds are members selected from the group consisting of triethylaluminum, triisobutylaluminum, diisobutylaluminum hydride, and diethylzinc.

6. A process as specified in claim 1 wherein said organonickel compound is a nickel salt of carboxylic acid containing from 4 to 30 carbon atoms.

7. A process as specified in claim 6 wherein said organonickel compound is selected from the group consisting of nickel benzoate, nickel naphthenate, nickel-2-ethylhexanoate, nickel neo-decanoate, nickel acetylacetonate, and nickel salicylaldehyde.

8. A process as specified in claim 1 wherein the mole ratio of the amount of organonickel compound added to the amount of cyclopentadiene present in said impure unsaturated $C_5$-hydrocarbon ranges from 0.3:1 to 20:1.

9. A process as specified in claim 8 wherein the mole ratio of the amount of organonickel compound added to the amount of cyclopentadiene present in said impure unsaturated $C_5$- hydrocarbon ranges from 2:1 to 10:1.

10. A process as specified in claim 9 wherein the mole ratio of the amount of organonickel compound added to the amount of cyclopentadiene present in said impure unsaturated $C_5$-hydrocarbon ranges from 3:0 to 6:1.

11. A process as specified in claim 1 wherein the mole ratio of said members selected from the group consisting of triethylaluminum, triisobutylaluminum, diisobutylaluminum hydride, and diethylzinc to said organonickel compound ranges about 1:1 to about 10:1.

12. A process as specified in claim 11 wherein the mole ratio of said members selected from the group consisting of triethylaluminum, triisobutylaluminum, diisobutylaluminum hydride, and diethylzinc to said organonickel compound ranges from 2:1 to 6:1.

13. A process as specified in claim 12 wherein the mole ratio of said members selected from the group consisting of triethylaluminum, triisobutylaluminum, diisobutylaluminum hydride, and diethylzinc to said organonickel compound ranges from 3:1 to 5:1.

14. A process as specified in claim 1 wherein said process is carried out at a temperature ranging from about −20° C. to about 150° C.

15. A process as specified in claim 14 wherein said process is carried out at a temperature ranging from about 15° C. to 60° C.

16. A process as specified in claim 1 wherein said $C_5$-hydrocarbon is selected from the group consisting of isoprene and piperylene.

17. A process for the purification of impure unsatureated $C_5$-hydrocarbons containing cyclopentadiene as an impurity comprising (1) adding to said impure unsaturated $C_5$-hydrocarbon (a) at least one member selected from the group consisting of trialkylaluminum compounds, dialkylaluminum hydride compounds, dialkylmagnesium compounds, and dialkylzinc compounds; and (b) an organonickel compound, in amounts and under conditions sufficient to convert the cyclopentadiene to a cyclopentadiene reaction product; followed by (2) fractionally distilling said impure unsaturated $C_5$-hydrocarbon under conditions sufficient to separate the cyclopentadiene reaction product from the $C_5$-hydrocarbon.

* * * * *